US00PP13468P3

(12) United States Plant Patent
Strope

(10) Patent No.: US PP13,468 P3
(45) Date of Patent: Jan. 14, 2003

(54) NEW GUINEA IMPATIENS PLANT NAMED 'BALCEBLICOL'

(75) Inventor: Kerry M. Strope, Pismo Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 1 days.

(21) Appl. No.: 09/772,602

(22) Filed: Jan. 30, 2001

(65) Prior Publication Data

US 2002/0138890 P1 Sep. 26, 2002

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct New Guinea impatiens cultivar named Balceblico, characterized by its large light coral flowers, striking bronze foliage with yellow/orange variegation, compact, upright and mounded habit and excellent basal branching.

1 Drawing Sheet

BACKGROUND OF THE INVENTION

The present invention comprises a new and distinct New Guinca impatiens plant, botanically known as *Impatiens hawkeri*, and hereinafter referred to by the cultivar name 'Balceblico'.

The new cultivar was developed by the inventor through a controlled breeding program during 1997 in Arroyo Grande, Calif. The objective of the breeding program was to develop cultivars with numerous large flowers, compact to moderate growth habit and excellent basal branching.

The female (seed) parent of 'Balceblico' was the proprietary *Impatiens hawkeri* cultivar designated '50-4' (non-patented), characterized by its pink flowers, compact habit and dark green foilage. The male (pollen) parent of 'Balceblico' was the proprietary *Impatiens hawkeri* cultivar designated '1578' (non-patented), characterized by its salmon flowers, compact habit and dark green variegated foliage. 'Balceblico' was discovered and selected as a flowering plant within the progeny of the stated cross by the inventor in December of 1997.

Asexual reproduction of the new cultivar by terminal or stem cuttings has demonstrated that the characteristics of the new cultivar as herein described are firmly fixed and are retained through successive generations of such asexual propagation. 'Balceblico' has been asexually reproduced in Arroyo Grande, Calif. and West Chicago, Ill.

SUMMARY OF INVENTION

It was found that the cultivar of the present invention:

(a) Exhibits large round light coral flowers, (b) Forms bronze foilage with yellow/orange variegation, (c) Exhibits a good basal branching character, and (d) Exhibits an upright mounded growth habit.

The new cultivar of the present invention can be compared to Celebration Deep Coral (U.S. Plant Pat. No. 9,214). In side by side comparisons, plants of the new cultivar differ from plants of Celebration Deep Coral by the following characteristics: it is found that the new cultivar is more compact, has larger flowers that are more orange in color and different foliage variegation. A detailed comparison can be found in Table A, below.

TABLE A

| CHARACTERISTIC | 'BALCEBLICO' | CELEBRATION DEEP CORAL |
|---|---|---|
| PLANT HEIGHT | 19.6 cm | 27.1 cm |
| NUMBER OF BRANCHES | 8.5 | 9 |
| BRANCH LENGTH | 15.4 cm | 23.3 cm |
| BRANCH DIAMETER | .8 cm | .9 cm |
| INTERNODE LENGTH | 4.1 cm | 5.8 cm |
| BUD LENGTH | 2.1 cm | 2.2 cm |
| BUD DIAMETER | 1.3 cm | 1.3 cm |
| PEDUNCLE LENGTH | 4.4 cm | 4.9 cm |
| FLOWER DIAMETER | 7.2 cm | 6.8 cm |
| PETAL COLOR-FULLY OPENED-UPPER SURFACE | BETWEEN 41A & 41B WITH "EYE" OF BETWEEN 60C & 60D | 50 A |
| SPUR LENGTH | 4.9 cm | 5.2 cm |
| SPUR COLOR | LIGHTER THAN 60D | 53 C |
| MATURE LEAF COLOR-UPPER SURFACE | 200A AT EDGES; MIXTURE OF 170A AND 167A WITH VEINATION OF 187D | 187A WITH MIDRIB OF 45B AND 19A |
| LEAF LENGTH × WIDTH | 8.1 × 2.5 cm | 8.4 × 3.5 cm |
| PETIOLE LENGTH | .6 cm | .9 cm |

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown in a greenhouse at West Chicago, Ill., U.S.A.

DETAILED DESCRIPTION

The 'Balceblico' cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Aug. 30, 2000 between 9:00 and 9:30 am under natural daylight. The plants were ten (10) weeks old and were produced from cuttings taken from stock plants and were grown in 10 cm pots under greenhouse conditions comparable to those used in commercial practice while utilizing a soilless growth medium and maintaining temperatures of approximately 72° F. during the day and approximately 65° F. during the night.

Classification:

*Botanical.*—*Impatiens hawkeri* cultivar 'Balceblico'.

Parantage: Proprietary seedling '50-4' (seed)×Proprietary seedling '1578' (pollen).

Propagation:

*Type cutting.*—Terminal tip.

*Time to initiat roots.*—Approximately 7–14 days with the shorter times generally being experienced in the summer and the longer times in the winter.

*Time to develop roots.*—Approximately 21 days.

*Rooting habit.*—Fibrous, branching.

Plant description:

*Habit of growth.*—Moderately vigorous with good basal branching. A mature plant, at 8 to 10 weeks after the planting of a rooted cutting, commonly measures approximately 19.6 cm in height and approximately 25.6 cm in width.

*Plant form.*—Upright and mounded.

*Foliage.*—Leaves are lanceolate, with acuminate apex. attenuate base and serrate, ciliate margin. Size of mature foliage: approximately 8.1 cm in length and approximately 2.5 cm in width. Petiole length is approximately 6 mm. Color of upper surface of mature leaves: closest to 200A at edges, areas of 170A and 167A within the midsection and venation of 187D; lower surface: closest to 187B at edges, 187D in midsection and venation of 185B.

*Stem.*—Color:187B; Internode length: approximately 4.1 cm.

Flower description:

*Flowering habit.*—Freely flowering.

*Natural flowering season.*—Year round in greenhouse environment. Flowering is continuous from spring until fall in the garden.

*Bud shape, size, color.*—Shape: Ovate Length: 1.7 cm. Diameter: 1 cm. Color: 39D.

*Flowers borne.*—Above foliage arising from leaf axils.

*Flower color.*—Upper surface of petals is between 41A and 41B, with each petal having attachment points of between 60C and 60D with darkest area at base of lower two petals, forming an "cyc", lower surface of petals is between 43D and 44D with base and midvein of 60D.

*Quantity of flowers.*—Approximately 3 flowers and 4 buds per stem.

*Petals.*—Number: Five, Shape: Obovate Size: Superior petal: width — 4.2 cm. length — 2.9 cm; lateral petals: length — 3.1 cm, width — 2.9 cm.; lower petals: length — 3.9 cm. width — 3.7 cm.

*Upper and lower surface texture of leaf and petal.*—All surfaces are smooth.

*Flower diameter.*—Approximately 7.2 cm.

*Spur.*—Approximately 4.9 cm in length; lighter than 60D in color. Shape: Slightly curved.

*Peduncle.*—*Length: Approximately* 4.4 cm. Color. 185A.

*Reproductive organs.*—Androccium: The anthers are fused together forming one organ that surrounds the pistil. Generally, the anthers shed pollen prior to the stigma becoming receptive. The pollen color is 19D. Gynoecium: the stigma color is pale purple, style color is 144A and the ovary color is 144A.

*Stamen number, anther shape, size, color.*—Stamen number: 4. Anther shape: Hooded. Anther size: 2.5 mm. Anther color: 39B.

*Pistil number, length, stigma color.*—Pistil number: 1. Length: 5 mm. Color: Transparent (colorless).

*Seed development.*—Seed production has not been observed.

*Disease resistance.*—Resistance to pathogens has not been observed.

I claim:

1. A new and distinct cultivar of New Guinea Impatiens plant named 'Balcelblico' substantially as herein shown and described, which:

(a) Exhibits large round light coral flowers.

(b) Forms bronze foliage with yellow/orange variegation, (c) Exhibits a good basal branching character, and (d) Exhibits an upright mounded growth habit.

* * * * *

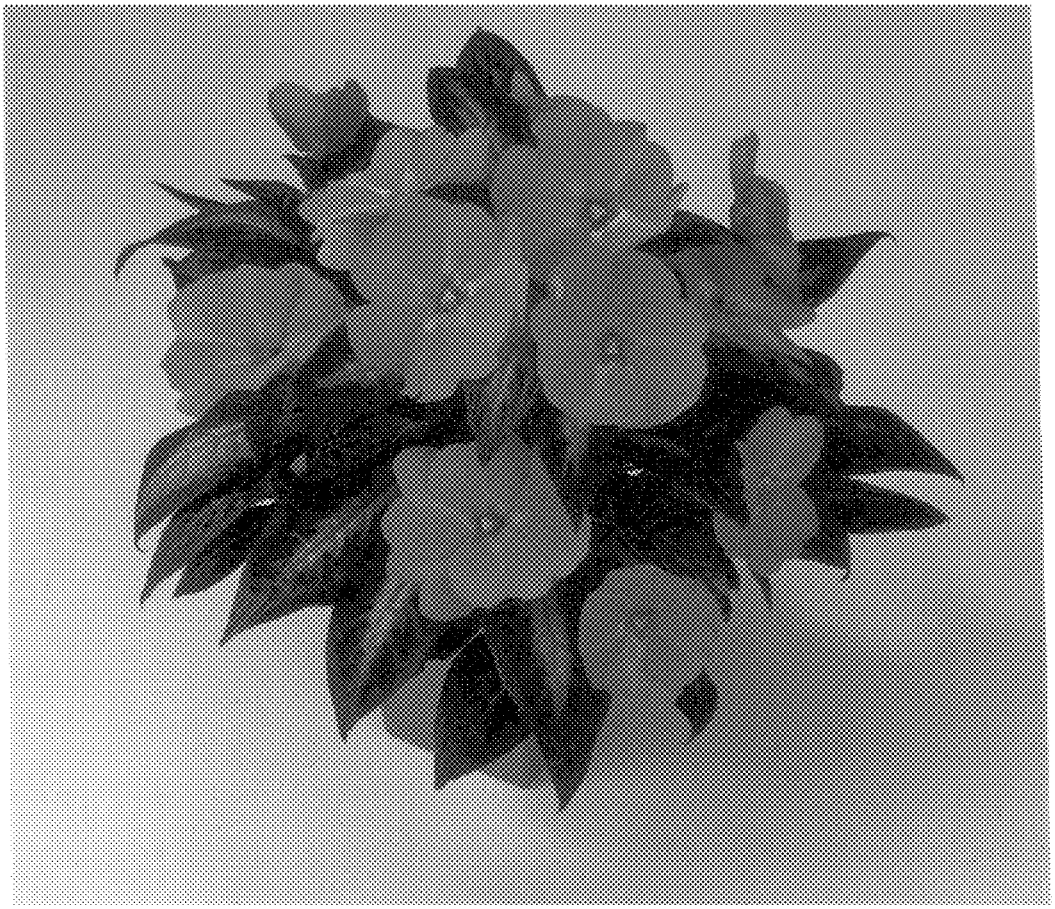

UNITED STATES PATENT AND TRADEMARK OFFICE

CERTIFICATE OF CORRECTION

PATENT NO. : PP 13,468 P3
DATED : January 14, 2003
INVENTOR(S) : Kerry M. Strope It is certified that error appears in the above-identified patent and that said Letters Patent is hereby corrected as shown below:

Title page,
Item [54], The title should read: -- NEW GUINEA IMPATIENTS PLANT NAMED 'BALCEBLICO' --

Signed and Sealed this

Seventeenth Day of June, 2003

JAMES E. ROGAN
*Director of the United States Patent and Trademark Office*